US008521325B2

(12) United States Patent
Shibata

(10) Patent No.: US 8,521,325 B2
(45) Date of Patent: Aug. 27, 2013

(54) DRUG DELIVERY DEVICE AND DRUG DELIVERY METHOD

(75) Inventor: Shoji Shibata, Ehime (JP)

(73) Assignee: Panasonic Corporation, Osaka (JP)

( * ) Notice: Subject to any disclaimer, the term of this patent is extended or adjusted under 35 U.S.C. 154(b) by 210 days.

(21) Appl. No.: 12/995,811

(22) PCT Filed: Sep. 11, 2009

(86) PCT No.: PCT/JP2009/004546
§ 371 (c)(1),
(2), (4) Date: Dec. 2, 2010

(87) PCT Pub. No.: WO2010/032411
PCT Pub. Date: Mar. 25, 2010

(65) Prior Publication Data
US 2011/0087368 A1    Apr. 14, 2011

(30) Foreign Application Priority Data

Sep. 19, 2008    (JP) ................................ 2008-241839

(51) Int. Cl.
*G06F 17/00* (2006.01)
(52) U.S. Cl.
USPC ............ 700/240; 700/242; 700/236; 700/244
(58) Field of Classification Search
USPC .................. 700/236, 242, 244, 240
See application file for complete search history.

(56) References Cited

U.S. PATENT DOCUMENTS

| 5,604,692 | A | * | 2/1997 | Yuyama | ......................... 700/240 |
| 5,988,858 | A | * | 11/1999 | Yuyama et al. | ............... 700/230 |
| 6,181,979 | B1 | * | 1/2001 | Murakami | ..................... 700/216 |
| 6,701,218 | B2 | * | 3/2004 | Koike et al. | ................... 700/235 |
| 7,775,756 | B2 | * | 8/2010 | Koike et al. | ............. 414/331.11 |
| 8,091,213 | B2 | * | 1/2012 | Yuyama et al. | ............... 700/237 |
| 2002/0063698 | A1 | | 5/2002 | Koike et al. | |

FOREIGN PATENT DOCUMENTS

| CA | 2 363 635 | 5/2002 |
| JP | 7-88156 | 4/1995 |
| JP | 2005-161736 | 6/2005 |
| JP | 2005-279268 | 10/2005 |
| JP | 3722695 | 11/2005 |
| JP | 3737697 | 11/2005 |
| JP | 2006-109899 | 4/2006 |
| JP | 2006-109900 | 4/2006 |

OTHER PUBLICATIONS

International Search Report issued Jan. 12, 2010 in International (PCT) Application No. PCT/JP2009/004546.

* cited by examiner

*Primary Examiner* — Timothy Waggoner
(74) *Attorney, Agent, or Firm* — Wenderoth, Lind & Ponack, L.L.P.

(57) ABSTRACT

A drug delivery device (1) delivers a stored drug to a conveyance receptacle (T) adapted to be attached with a card (RC) that displays desired information. The drug delivery device (1) includes card processor (10), a label printer (6), and a controller (5). The card processor (10) enters patient identification information on the card (RC) and attaches the card (RC) to the conveyance receptacle (T). The label printer (6) prints a first label that displays the patient identification information and that is inserted into the conveyance receptacle (T). The controller (5) causes the label printer (6) to print the first label according to a state of the card processor (10). With the drug delivery device (1), identification information is applied more reliably and quickly to the conveyance receptacle by which the drug is delivered, and the efficiency of drug delivery is improved.

9 Claims, 15 Drawing Sheets

DRUG DELIVERY DEVICE AND DRUG DELIVERY METHOD

TECHNICAL FIELD

The present invention relates to a drug delivery device and a drug delivery method for delivering a drug stored in a cassette or the like.

BACKGROUND ART

There are conventional drug delivery devices with which ampoules, vials, plastic bottles, kits, bags, or the like containing a drug or the like are pre-loaded into a cassette and then delivered as needed.

FIG. 13 is an overall view of the configuration of a conventional drug delivery device 100 (see Patent Citation 1, for example).

The drug delivery device 100 has cassettes 102 containing a drug 104, a shelf 103 for holding the cassettes, and a device 105 for delivering the drug. The shelf 103 is divided laterally and longitudinally into numerous compartments, forming a plurality of cells 123. Each of the cells 123 holds a cassette 102 filled with the drug 104. A single cassette 102 is filled with several dozen (for example) units of the same type of drug 104.

The device 105 has an extractor 106 for extracting a drug from the cassette 102. The extractor 106 is controlled by a specific control device, and moves in the directions of the arrows 12A and 13A in the drawing. The extractor 106 is positioned on a rear face 3B of the holding shelf with respect to the cassette 102 containing the desired drug 104. The extractor 106 has a unit similar to a known robot arm (not shown). The robot arm takes the drug 104 out of the cassette 102 and delivers it to a delivery tray 141.

The delivery tray 141 is divided into a plurality of regions by partition plates 142. The drug that is to be delivered is delivered to each region according to drug administration zones. The delivery tray 141 by which the drug 104 is delivered is transported to the drug administration site, such as a hospital ward.

As discussed above, with a conventional drug delivery device, ampoules or the like of drug are stored in trays (conveyance receptacles) for each patient and transported to each patient. The trays must display information that identifies the patients. This is so that the stored drug or the like will be handed to the correct patient, or used on the correct patient.

One display means for identifying the trays (conveyance receptacles) is a display label.

The display label is a label having a label paper or a self-adhesive label with patient identification information or the like printed on. The display label is attached by hand to one side of a tray, and is removed by hand when the tray is no longer needed. However, the attachment and removal of the display labels and so forth can entail a great deal of work, and for this and other reasons, the use of rewritable cards that can be written to repeatedly is known (see Patent Citation 2, for example).

FIG. 14 shows a conventional drug delivery device 200 with which cards (display members) are automatically and removably attached to trays.

The drug delivery device 200 has a card attachment and removal conveyance means 210 and a writing means 220. The card attachment and removal conveyance means 210 conveys a rewritable card 201, which is attached to or removed from a tray T, between the tray T and the writing means 220. The writing means 220 writes patient information on the rewritable card 201. The writing means 220 is connected to the card attachment and removal conveyance means 210.

With the drug delivery device 200 above, when a tray T that has been transported in comes to a stop, the rewritable card 201 attached to that tray is removed by the card attachment and removal conveyance means 210. The removed rewritable card 201 is sent between plastic rollers and rubber rollers 212 of the card attachment and removal conveyance means 210, and conveyed to the writing means 220. The conveyed rewritable card 201 is printed by the writing means 220, sent back along the rubber rollers 212 and the plastic rollers, and attached to the tray T by the card attachment and removal conveyance means 210.

PRIOR ART PUBLICATIONS

Patent Citations

Patent Citation 1: Japanese Laid-Open Patent Application 2006-109900
Patent Citation 2: Japanese Laid-Open Patent Application 2005-279268

DISCLOSURE OF INVENTION

Technical Problem

With the card attachment and removal unit of the above-mentioned drug delivery device, the rewritable card is physically attached to the tray T. Accordingly, there may be situations in which the position of the card becomes misaligned during transport or during attachment or removal of the card, or situations in which the card cannot be properly inserted into the writing means or a card holder of the tray. Also, if a rewritable card is not in the card holder of the tray, the rewritable card must be put in place manually. If this happens and the device is temporarily stopped, it takes a long time before the device is restored to its normal state, so delivery of the drug is inefficient. Also, when the rewritable card is put in place manually after the completion of delivery without stopping the device, then it takes a long time to find the tray with no rewritable card, and it is possible that the operator may forget to put the rewritable card in place. Situations such as these result in low drug delivery efficiency, so a drug cannot be administered to a patient on time.

It is an object of the present invention to provide a drug delivery device and a drug delivery method with which identification information can be applied more reliably and quickly to the conveyance receptacle by which the drug is delivered, and the efficiency of drug delivery can be improved.

Technical Solution

The drug delivery device pertaining to a first aspect of the invention is a drug delivery device that delivers a stored drug to a conveyance receptacle adapted to be attached with a card that displays desired information, said drug delivery device comprising a card processor, a label printer, and a controller. The card processor enters patient identification information on the card and attaches the card to the conveyance receptacle. The label printer prints a first label configured to display the patient identification information and to be inserted into the conveyance receptacle. The controller causes the label printer to print the first label according to a state of the card processor.

The "drug" referred to here is a drug that can be prescribed, such as an injection drug, an oral drug, an ointment, a plaster, a suppository, or the like. Examples of the "patient identification information" include the patient's name, ID number, sex, date of birth, department name, hospital ward name, and room number. The cards that are processed by the card processor may be ones that have been attached to individual conveyance receptacles ahead of time, or may be ones taken from a card holder or the like.

Here, a first label is selectively printed by the label printer according to the state of the card processor. The "first label" is a label adapted to be attached to the conveyance receptacle instead of a card. If the card processor is in a normal state, the controller does not cause the label printer to print the first label but only causes the card processor to print a card. On the other hand, if the card processor is not in a normal state, the controller determines whether or not to cause the label printer to print a first label.

The phrase "when the card processor is not in a normal state" refers, for example, to a situation in which an error has occurred in the card processor itself, a situation in which patient identification information cannot be displayed on a card, a situation in which the card processor cannot remove a card from a conveyance receptacle, and a situation in which a card cannot be attached to a conveyance receptacle.

Consequently, even though there is the possibility of failure to attach a card to a conveyance receptacle, since a label that serves in the stead of that card is automatically printed, the efficiency of drug delivery will be improved.

The drug delivery device pertaining to a second aspect of the invention is the drug delivery device pertaining to the first aspect, wherein the card is a rewritable card.

The "rewritable card" referred to here is a card that can be rewritten. Examples of rewritable card include leuco cards that change color when a leuco dye in the recording layer reacts and bonds with a developer, and what are known as light-scattering rewritable cards. For instance, with a leuco rewritable card, information can be rewritten by taking advantage of the properties of coloration (bonding of the dye and the developer) by high-temperature heating and rapid cooling, and erasure (separation of the dye and the developer) by low-temperature heating and gradual cooling.

A rewritable card that allows the card to be rewritten is utilized here. Consequently, a card that has been inserted in the conveyance receptacle can be used again while still attached to the conveyance receptacle during the next time a drug is delivered, which eliminates the trouble of having to reinsert a new card, etc.

The drug delivery device pertaining to a third aspect of the invention is the drug delivery device pertaining to the first or second aspect, wherein the label printer further prints a second label configured to display the patient identification information and drug administration information and to be inserted into all conveyance receptacles.

The "drug administration information" referred to here includes the name of the drug to be administered to a patient, the amount of drug, the administration date and time, and so forth. Also, the second label may be printed integrally with the first label, or may be printed separately.

Here, the label printer always prints a second label and places it in the conveyance receptacle, so the first label can be additionally printed and placed in a conveyance receptacle along with the second label, for example. Therefore, even if a first label is printed according to the state of the card processor, there is no need for significant modification of the control or operation of the label printer.

The drug delivery device pertaining to a fourth aspect of the invention is the drug delivery device pertaining to any of the first to third aspects, wherein the controller causes the label printer to print the first label when an error occurs in the card processor.

The phrase "when an error occurs in the card processor" here includes, for example, situations in which all or part of the card processor malfunctions, and in which it comes to a stop in mid-operation.

Here, when an error occurs in the card processor itself, the controller causes the label printer to print a first label. Consequently, it is reliably detected whether there is a high likelihood of failure to attach the card, and a first label can be printed and attached to the conveyance receptacles instead of a card.

The drug delivery device pertaining to a fifth aspect of the invention is the drug delivery device pertaining to any of the first to fourth aspects, wherein the card processor has a card detector configured to detect a card at a specific location, and the controller causes the label printer to print the first label when the detector does not detect the card.

The "card detector" referred to here is, for example, a CCD camera or an optoelectric sensor having a light projecting and receiving element. The "specific location" is, for example, the location of the card before it is taken out of the conveyance receptacle and the patient identification information is displayed, or the location of the card before the patient identification information is displayed and the card is attached to the conveyance receptacle. Thus, by detecting whether or not the card is present at each specific location, the controller ascertains that there is a high likelihood that the card on which the patient identification information is displayed will not be attached to the conveyance receptacle, and prints a first label that will serve in the stead of the card.

Consequently, it is to be reliably detected when there is a high likelihood of failure to attach a card, and a first label can be printed and attached to the conveyance receptacle.

The drug delivery device pertaining to a sixth aspect of the invention is the drug delivery device pertaining to any of the first to fifth aspects, further comprising a card holder configured to hold extra cards to be supplied to the card processor, wherein the controller supplies the extra cards to the card processor from the card holder.

The "extra cards" here are cards that are readied separately from the cards attached to the conveyance receptacle.

Here, the controller supplies an extra card when, for example, a card could not be taken out of the conveyance receptacle. This prevents the card from being missing.

The drug delivery device pertaining to a seventh aspect of the invention is the drug delivery device pertaining to the sixth aspect, wherein the controller does not cause the label printer to print the first label when any of the extra cards is supplied.

Here, if any of the extra cards is supplied, the label printer does not print a first label. This prevents labels from being printed more often than necessary.

The drug delivery device pertaining to an eighth aspect of the invention is the drug delivery device pertaining to the sixth aspect, wherein the controller causes the label printer to print the first label when any of the extra cards is supplied.

Here, the label printer prints a first label even when any of the extra cards is supplied. Consequently, even if the likelihood of failure to attach the card is low, a first label will be printed and attached to the conveyance receptacle, which improves safety.

The drug delivery device pertaining to a ninth aspect of the invention is the drug delivery device pertaining to the first or eighth aspect, further comprising a unit configured to remove the card attached to the conveyance receptacle for which the first label has been printed when the first label is printed by the label printer.

Here, a card attached to a conveyance receptacle for which a first label was printed by the label printer is removed. This prevents both a card and a first label from being applied one over the other to the conveyance receptacle. Also, the card can be removed for the sake of safety in the event that the wrong information or the like is displayed on a card processed by the card processor, or in the event that the wrong card has been attached, for example.

The drug delivery method pertaining to a tenth aspect of the invention is a drug delivery method of delivering a stored drug to a conveyance receptacle adapted to be attached with a card that displays desired information, said drug delivery method comprising a card processing, a label printing, and a controlling. In the card processing, patient identification information is entered on the card and the card is attached to the conveyance receptacle. In the label printing, a first label configured to display the patient identification information is printed and inserted into the conveyance receptacle. In the controlling, the label printing is executed and a first label is printed according to a state in the card processing step.

Here, in the controlling, the label printing is executed and a first label is printed according to a state in the card processing. Consequently, even if there is a risk of failure to attach a card to a conveyance receptacle, a first label can be automatically printed instead of the card, so the efficiency of drug delivery can be improved.

Advantageous Effects

With the drug delivery device and drug delivery method pertaining to the present invention, identification information is applied more reliably and quickly to the conveyance receptacle by which the drug is delivered, and the efficiency of drug delivery is improved.

BEST MODE FOR CARRYING OUT THE INVENTION

1. First Embodiment

The drug delivery device 1 pertaining to an embodiment of the present invention will be described through reference to FIGS. 1 to 12.

In the following description, the term "drug" is a drug that can be prescribed, such as an injection drug, an oral drug, an ointment, a plaster, a suppository, or the like.

1.1. Overall Configuration of Drug Delivery Device 1

Figure 1:
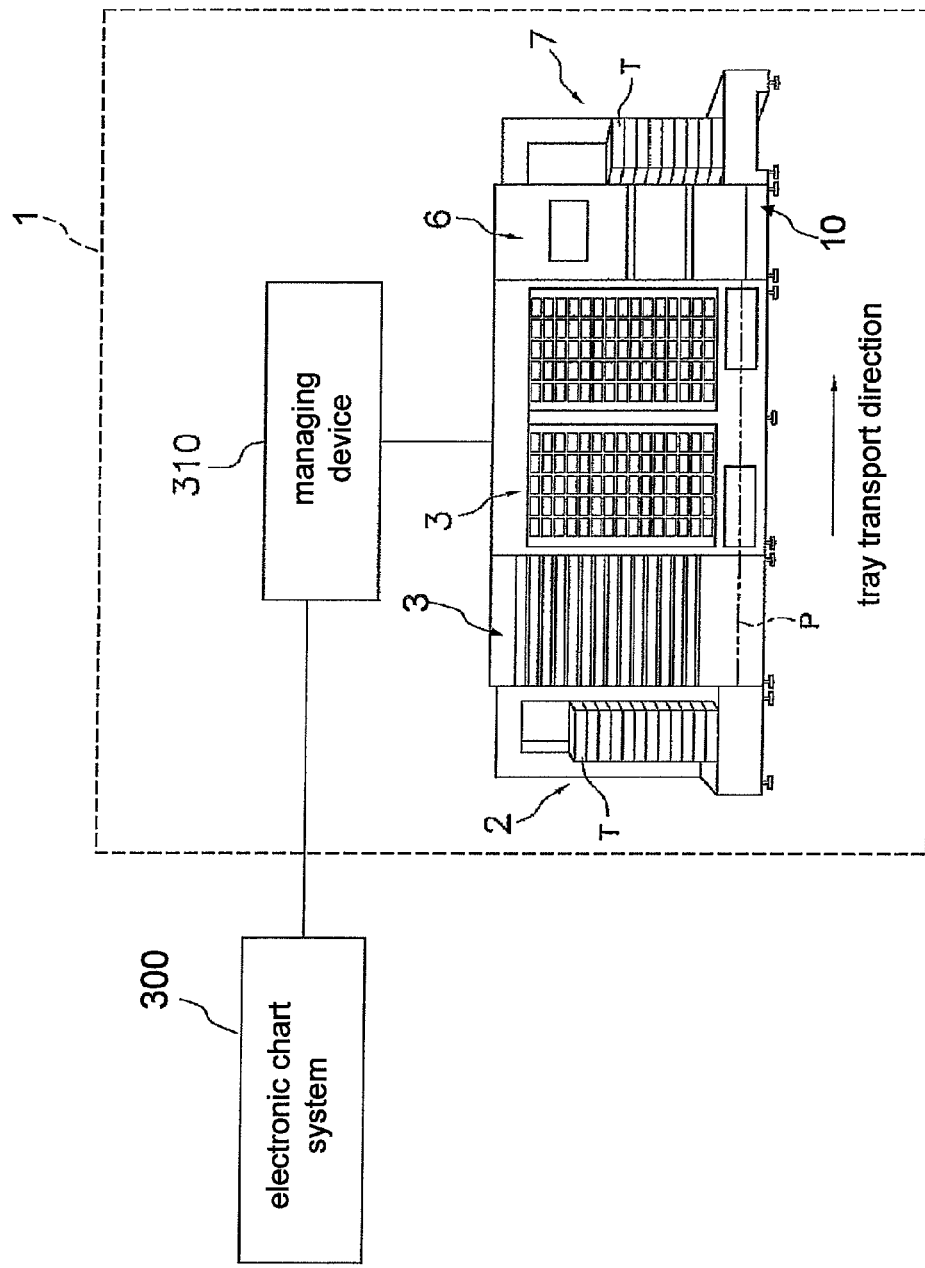
FIG. 1 is an overall view of the drug delivery device pertaining to an embodiment.

FIG. 1 shows an overall view of the drug delivery device 1 pertaining to this embodiment.

Figure 2:
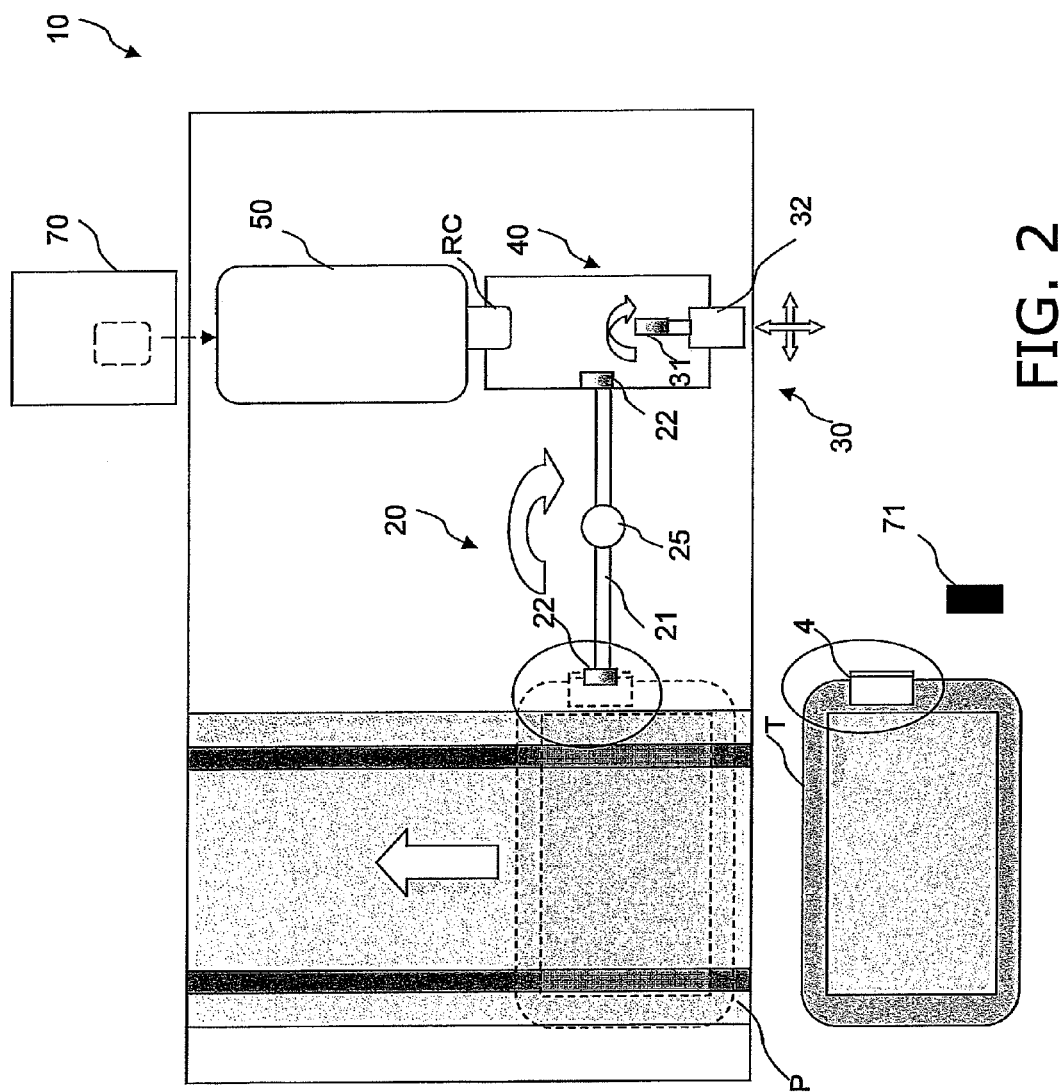
FIG. 2 is a top view of the card processing unit pertaining to this embodiment.

The drug delivery device 1 performs drug delivery processing according to patient identification information, drug administration information, prescription information, and so forth. Also, as shown in FIG. 2, the drug delivery device 1 recovers an unwritten rewritable card RC (hereinafter referred to as "unprinted rewritable card RC") from each tray (conveyance receptacle) T that is transported in, and at the same time automatically attaches a written rewritable card RC (hereinafter referred to as "printed rewritable card RC") with a card processing unit 10 (FIG. 2) to each tray T.

Figure 15B:
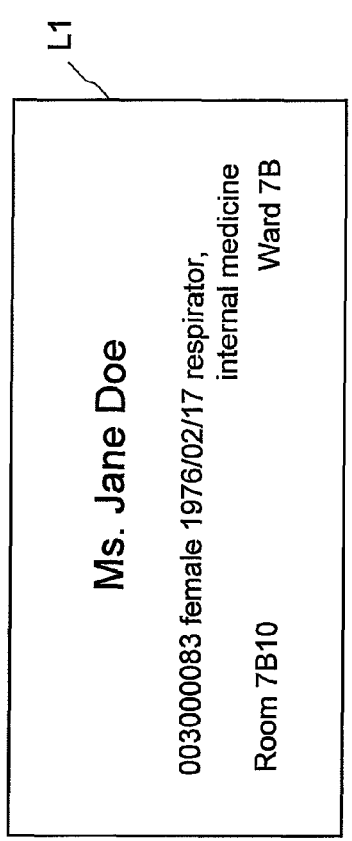
FIGS. 15A-15C illustrate an example of the card, tray label, and drug administration label pertaining to this embodiment.
Figure 15C:
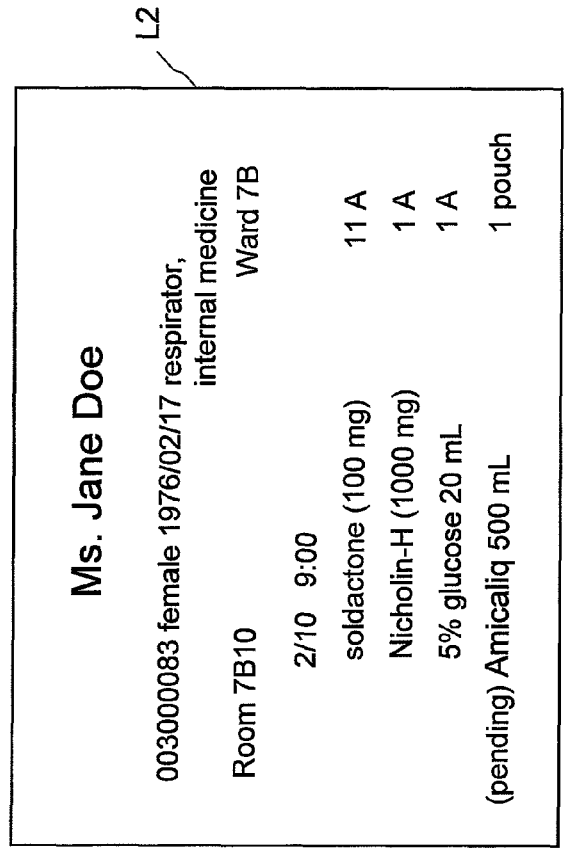
Figure 15A:
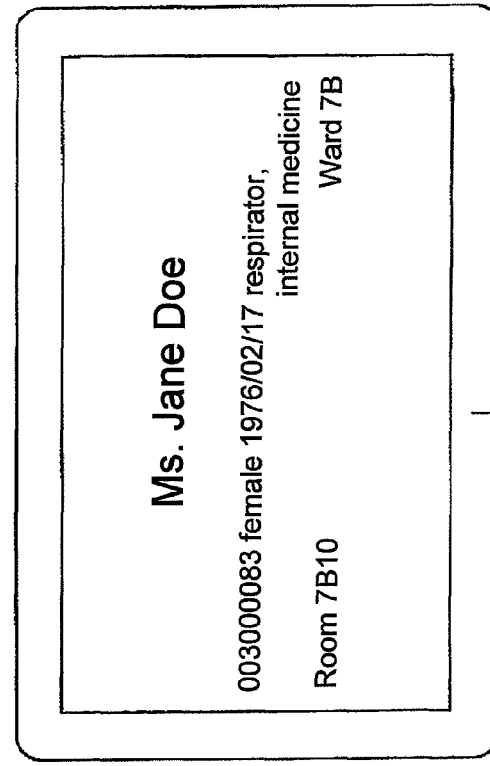

Various patient identification information, drug administration information, prescription information, and so forth is sent from an electronic chart system 300 to a server or other such managing device 310. Examples of patient identification information include the patient's name, ID number, sex, date of birth, department name, hospital ward name, and room number, and this information is displayed on a rewritable card RC, a tray label L1, a drug administration label L2, a prescription, or the like (FIGS. 15A, 15B and 15C). The drug administration information is the name of the drug to be administered to a patient, the amount of the drug, the administration date and time, and so forth, and this information is displayed mainly on the drug administration label L2. Prescription information is the details of what is written on the prescription, and includes patient identification information as well as the name of the prescribed drug, its dosage, the administration date and time, the amount to be taken each time, the administration method, and so forth. These different kinds of information are not strictly categorized, and there may be some overlap in all or part of the information.

The patient identification information, drug administration information, prescription information, and so forth are sent form the electronic chart system 300 to the managing device 310.

The trays T that are transported are A4 or A3-size holders. An unprinted rewritable card RC is attached to a card holder 4 (FIG. 3) as discussed below for each tray T prior to transport.

Figure 3:
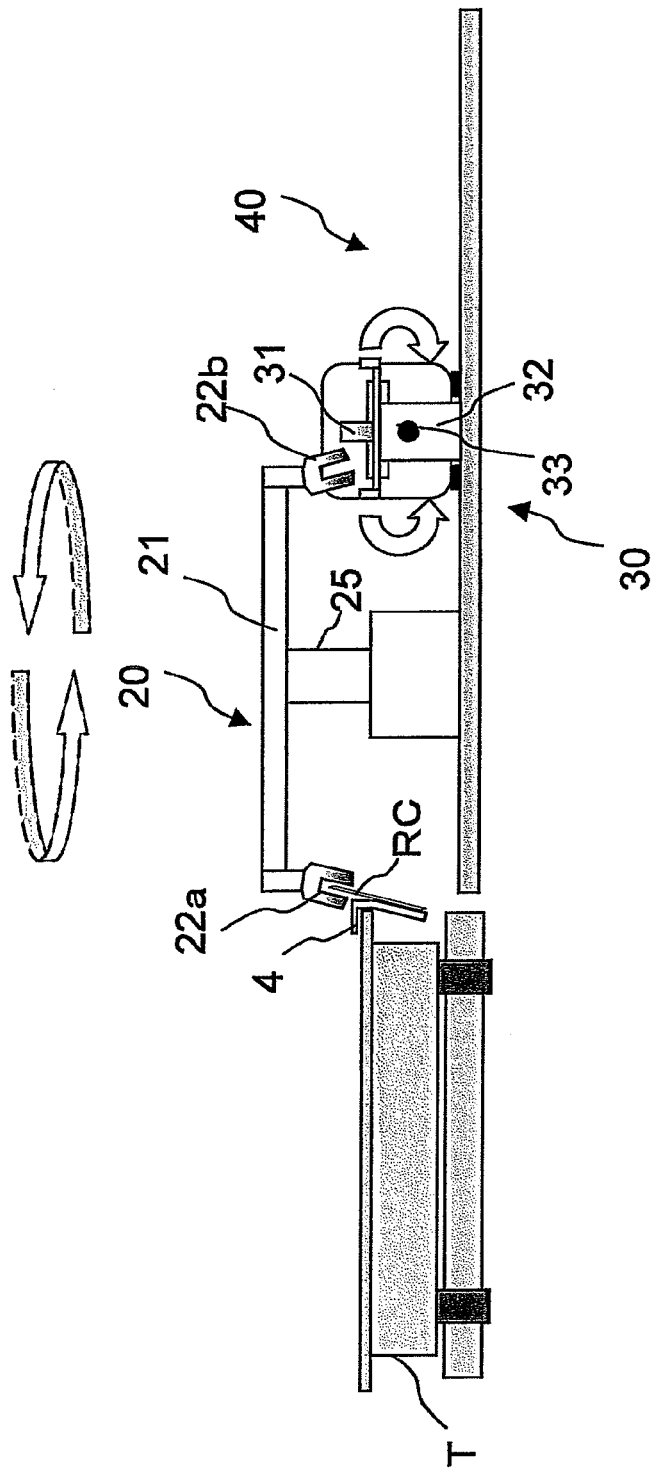
FIG. 3 is a front view of the card processing unit pertaining to this embodiment.

As shown in FIG. 3, the card holder 4 is attached at one end on the card processing unit 10 side of the tray T. As also shown in FIG. 3, the card holder 4 is formed so that its upper part is inclined to the card processing unit 10 side with respect to the vertical face of the tray T. The card holder 4 is open at the top, and a rewritable card RC is inserted into this opening. The card holder 4 is also open on the sides, so the rewritable card RC may instead be inserted from the side.

The rewritable card RC is a card that can be rewritten. Examples of rewritable card include leuco cards that change color when a leuco dye in the recording layer reacts and bonds with a developer, and what are known as light-scattering rewritable cards. For instance, with a leuco rewritable card, information can be rewritten by taking advantage of the properties of coloration (bonding of the dye and the developer) by high-temperature heating and rapid cooling, and erasure (separation of the dye and the developer) by low-temperature heating and gradually cooling. However, some other card-shaped object with which a display can be changed can be used instead of a rewritable card. As shown in FIG. 15A, what is mainly printed on the rewritable card RC is patient identification information.

This drug delivery device 1 primarily comprises a tray supply unit 2, a drug delivery unit 3, a tray transport path P, a label/prescription printing unit (label printer) 6 (FIG. 7), a completed tray stacking unit 7, and a card processing unit (card processor) 10. The drug delivery device 1 also comprises a device controller 5 and a managing device 310 (FIG. 8) as controllers, which control the various units.

The tray supply unit 2 sends out the stacked trays T one at a time into the tray transport path P at a command from the device controller 5 of the drug delivery device 1. The trays T are transported in the direction of the arrow in FIG. 1 along the tray transport path P, and temporarily come to a stop at a specific position near the drug delivery unit 3.

The drug delivery unit 3 is disposed opposite the tray transport path P and downstream from the tray supply unit 2. The drug delivery unit 3 has a drug holding means such as cassettes or drawers for holding drugs, and a pickup means for automatically taking the drugs out of the drug holding means and delivering them into the trays T. The drugs are put in ampoules, vials, plastic bottles, kits, bags, or other such containers, and stored in the drug holding means. The pickup means is constituted by a robot arm or the like. The pickup means picks up a drug and delivers it to a tray T at a command from the device controller 5, based on individual patient identification information, prescription information, or the like.

The card processing unit 10 is disposed opposite the tray transport path P and downstream from the drug delivery unit 3. As will be discussed below, the card processing unit 10 takes out an unprinted rewritable card RC from a tray T, and automatically attaches a printed rewritable card RC to the tray T. The configuration of the card processing unit 10 will be discussed in detail below.

Figure 7:
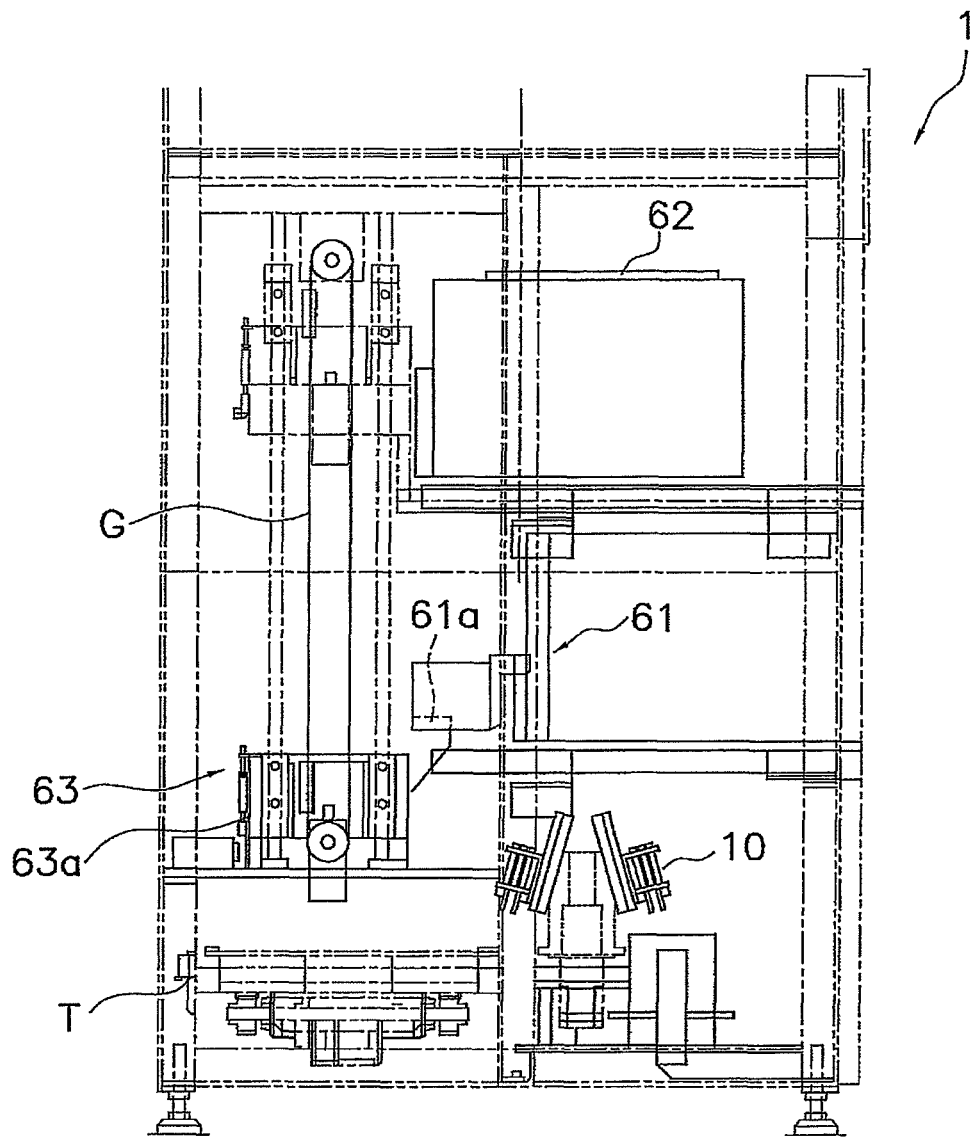
FIG. 7 is a see-through side view of the drug delivery device pertaining to this embodiment.

As shown in FIG. 7, the label/prescription printing unit 6 is disposed above the card processing unit 10. The label/prescription printing unit 6 prints out a drug administration label L2 (second label) and a prescription, and also selectively prints out a tray label L1 (first label), and inserts these into the tray T. The configuration of the label/prescription printing unit 6 will be discussed in detail below.

As shown in FIG. 15B, just as with the rewritable card RC, what is mainly printed on the tray label L1 is patient identification information. Also, as shown in FIG. 15C, the drug administration label L2 is printed not only with patient identification information, but also with drug administration information. If the tray label L1 and the drug administration label L2 are both printed, they may be printed on a single piece of paper that can be divided, or they may be printed on separate pieces of paper.

The completed tray stacking unit 7 stacks and holds trays T to which drugs, printed rewritable cards RC (or tray labels L1), drug administration labels L2, prescriptions, and so forth have been provided. The stacked trays T are conveyed by cart. The drugs in the trays T conveyed by cart go through drug inspection before being handed over to patients.

The drug delivery device 1 further comprises the device controller 5 (FIG. 8) and the managing device 310 that function as controllers.

The device controller 5 is a computer that controls the drug delivery device 1, and performs control of the tray supply unit 2, the drug delivery unit 3, the tray transport path P, the label/prescription printing unit 6, the completed tray stacking unit 7, the card processing unit 10, and so forth.

The managing device 310 is also a computer that controls the drug delivery device 1, and receives patient identification information, drug administration information, prescription information, and so forth from the electronic chart system 300, and issues commands to print rewritable cards RC, tray labels L1, drug administration labels L2, and prescriptions, and commands to supply rewritable cards RC, on the basis of the above information, a request from the device controller 5, etc.

The drug delivery device 1 pertaining to this embodiment will now be described while focusing on the control of the card processing unit 10 and the label/prescription printing unit 6, which are the characteristic components of the present invention.

1.2. Card Processing Unit 10

FIG. 2 is a schematic view of the card processing unit 10. The card processing unit 10 prints patient identification information on unprinted rewritable cards RC, and automatically attaches printed rewritable cards RC to trays T filled with drugs. The card processing unit 10 provides a means for more reliably attaching and removing rewritable cards RC to and from the trays T, and reducing as much as possible the time during which the trays T are stopped.

The card processing unit 10 has a handling mechanism 20, a card conveyance mechanism 30, a card position correcting mechanism 40, a card printing mechanism 50, and a card stocker (card holder) 70.

The handling mechanism 20 is disposed opposite the tray transport path P. The handling mechanism 20 replaces the unprinted rewritable cards RC inserted in the card holders 4 of the trays T with the printed rewritable cards RC held in the card conveyance mechanism 30.

The card conveyance mechanism 30 is disposed to the rear of the handling mechanism 20. The card conveyance mechanism 30 holds rewritable cards RC, turns them face up or down as necessary, and inserts or removes rewritable cards RC into or from the card printing mechanism 50.

As shown in FIG. 2, the card position correcting mechanism 40 is disposed in an L shape with respect to the handling mechanism 20. The card position correcting mechanism 40 performs planar positioning of the rewritable cards RC so as to sandwich both sides and the corners of the rewritable cards RC that have been placed substantially horizontally.

The card printing mechanism 50 is disposed contiguously with the card position correcting mechanism 40, and along with the card position correcting mechanism 40, forms the conveyance path of the rewritable cards RC that is parallel to the tray transport path P. The card printing mechanism 50 prints the patient identification information on the unprinted rewritable cards RC.

The card stocker 70 is disposed right after the card printing mechanism 50, and along with the card position correcting mechanism 40 and the card printing mechanism 50, forms the conveyance path of the rewritable cards RC that is parallel to the tray transport path P. The card stocker 70 stocks extra unprinted rewritable cards RC, and supplies unprinted rewritable cards RC to the card printing mechanism 50 as needed.

1.2.1. Handling Mechanism 20

Figure 4:
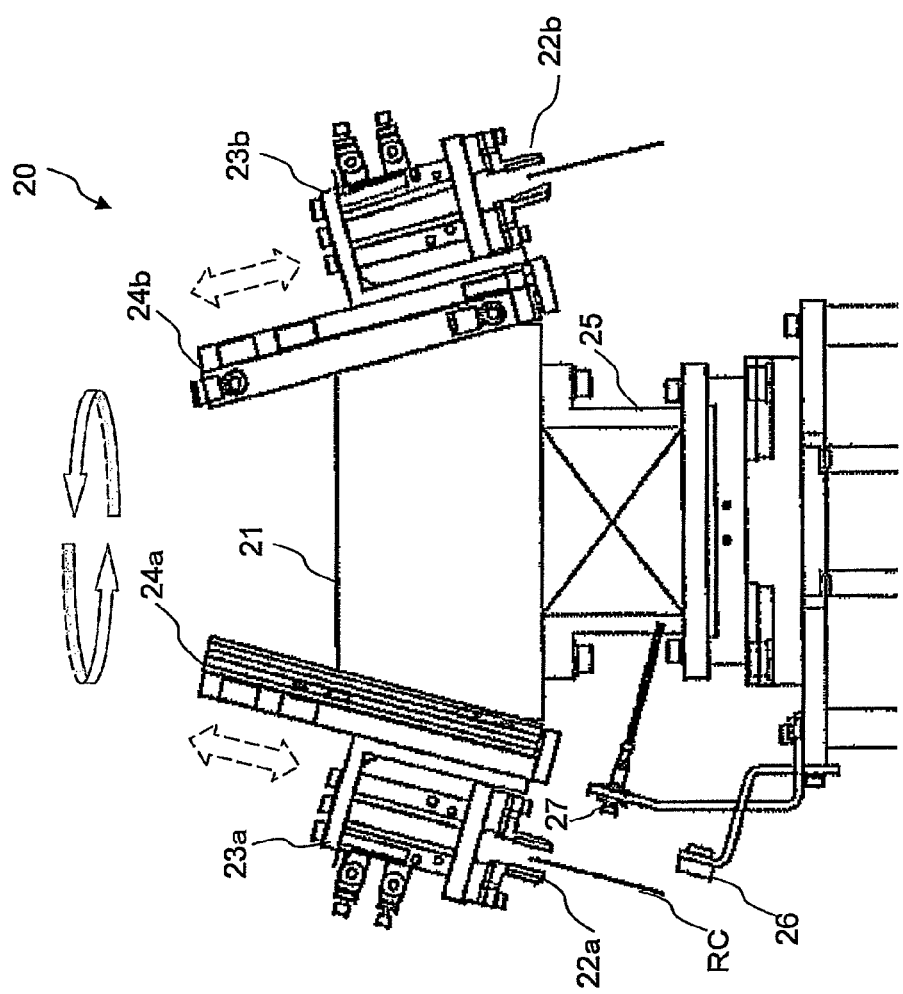
FIG. 4 is a front view of the handling mechanism pertaining to this embodiment.

As shown in FIG. 4, the handling mechanism 20 has an arm 21, a pair of card grippers 22a and 22b, a pair of supports 23a and 23b, a pair of guides 24a and 24b, a vertical rotation shaft 25, a first card sensor (card detector) 26, and a third card sensor 27.

The arm 21 is supported at its middle by the vertical rotation shaft 25, and the card grippers 22a and 22b are formed at the two ends of the arm.

The card grippers 22a and 22b are provided to the ends of the arm 21 so as to be able to clamp the edges of rewritable cards RC. The card grippers 22a and 22b are also formed so as to be inclined toward the vertical rotation shaft 25, matching the angle of the card holder 4 of the tray T.

The supports 23a and 23b support the card grippers 22a and 22b, and as shown by the arrows in FIG. 4, are formed so as to be able to move up and down along the guides 24a and 24b together with the card grippers 22a and 22b. The supports 23a and 23b are also formed so as to be inclined toward the vertical rotation shaft 25, just as are the card grippers 22a and 22b.

The guides 24a and 24b support the supports 23a and 23b on the arm 21. The guides 24a and 24b are also formed so as to be inclined toward the vertical rotation shaft 25, just as are the card grippers 22a and 22b and the supports 23a and 23b.

The vertical rotation shaft 25 supports the center of the arm 21 and has an axis that is substantially perpendicular to the plane on which the device is installed. As shown by the arrows in FIG. 4, the vertical rotation shaft 25 is formed so as to be able to rotate around this axis.

The first card sensor 26 is provided so as to be opposite the transport path P. The first card sensor 26 is, for example, an optoelectric sensor having a light projecting and receiving element. The first card sensor 26 mainly checks for the presence of a rewritable card RC in the card holder 4. The first card sensor 26 can detect, for example, that there is no unprinted rewritable card RC in the card holder 4, or that a printed rewritable card RC has fallen before being inserted into the card holder 4. The third card sensor 27 can detect that the card grippers 22a and 22b have missed gripping an unprinted rewritable card RC in the card holder 4 and dropped it. The first and third card sensors 26 and 27 send an error signal to the device controller 5 if a rewritable card RC cannot be sensed. The device controller 5 responds to this error signal by issuing a request to the managing device 310 to print a tray label L1, or issuing a request to supply an unprinted rewritable card RC, as discussed below.

The handling mechanism 20 operates as follows. A motor or other such drive component (not shown) provides drive at a command from the device controller 5, and the supports 23a and 23b are lowered along the guides 24a and 24b. The card grippers 22a and 22b, which descend along with the supports 23a and 23b, grasp an unprinted rewritable card RC held in the card holder 4 of the tray T, and a printed rewritable card RC held in the card conveyance mechanism 30, respectively. When the card grippers 22a and 22b have grasped the unprinted rewritable card RC and the printed rewritable card RC respectively, the supports 23a and 23b rise along the guides 24a and 24b. The vertical rotation shaft 25 then rotates 180 degrees. After this rotation, the supports 23a and 23b descend. The card gripper 22a then passes the unprinted rewritable card RC to the card conveyance mechanism 30, and the card gripper 22b inserts the printed rewritable card RC into the card holder 4 of the tray T.

1.2.2. Card Conveyance Mechanism 30

Figure 5:
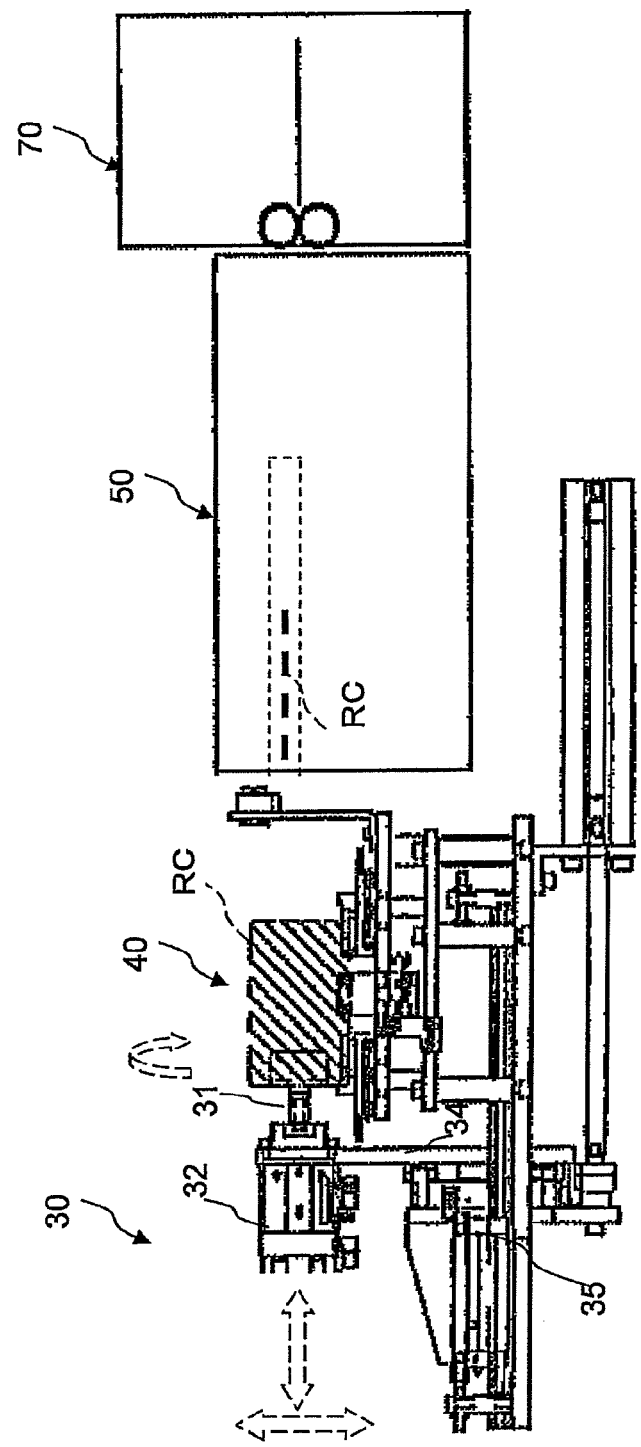
FIG. 5 is a side view of the card conveyance mechanism pertaining to this embodiment.

As shown in FIGS. 3 and 5, the card conveyance mechanism 30 has a card support 31, a support 32, a horizontal rotation shaft 33, a vertical guide 34, and a longitudinal guide 35.

The card support 31 is formed so as to be able to rotate around the horizontal rotation shaft 33, and grasps a rewritable card RC.

The support 32 is formed so as to support the card support 31 above the card position correcting mechanism 40. The support 32 is also formed so as to be able to be moved back and forth by the longitudinal guide 35 and moved up and down by the vertical guide 34.

The horizontal rotation shaft 33 has an axis that is substantially parallel to the plane on which the device is installed, and is formed so as to be able to rotate around this axis.

The vertical guide 34 is formed so as to guide the support 32 in the up and down direction of FIG. 5.

The longitudinal guide 35 is formed so as to guide the support 32 in the back and forth direction of FIG. 5, that is, the backward and forward direction with respect to the card printing mechanism 50.

The card conveyance mechanism 30 operates as follows.

As shown in FIGS. 3 and 5, the card support 31 receives unprinted rewritable cards RC grasped at an angle by the card grippers 22a and 22b of the handling mechanism 20. The card support 31 rotates around the horizontal rotation shaft 33 to put the rewritable card RC in a horizontal state, and then the support 32 is lowered by the driven vertical guide 34, which places the rewritable card RC in the card position correcting mechanism 40.

A second card sensor (card detector) 42 (FIG. 6) of the card position correcting mechanism 40 senses an unprinted rewritable card RC. The second card sensor 42 sends a card sensed signal to the device controller 5. In response, the device controller 5 issues a command to the card conveyance mechanism 30. The device controller 5 also directs the card conveyance mechanism 30 to flip the unprinted rewritable card RC over if needed.

After this, the card support 31 lets go of the unprinted rewritable card RC, and the unprinted rewritable card RC is positioned by the card position correcting mechanism 40. The position-corrected unprinted rewritable card RC is held by the card support 31, after which the card position correcting is released.

In a state in which the card support 31 is holding the unprinted rewritable card RC horizontal, the support 32 is raised by the driven vertical guide 34. The support 32 is then advanced by the driven longitudinal guide 35 toward the card printing mechanism 50. After the card support 31 lets go of the unprinted rewritable card RC, the unprinted rewritable card RC is inserted into the card printing mechanism 50 as indicated by the imaginary lines in FIG. 5.

When the printing of a rewritable card RC is finished, the card is ejected by the card printing mechanism 50, and the card support 31 grasps the printed rewritable card RC. The support 32 is retracted by the driven longitudinal guide 35, and the printed rewritable card RC is taken out of the card printing mechanism 50.

The support 32 is then lowered by the driven vertical guide 34, and the printed rewritable card RC is placed in the card position correcting mechanism 40. The card support 31 lets go of the printed rewritable card RC, and the printed rewritable card RC is positioned by the card position correcting mechanism 40. The position-corrected printed rewritable card RC is held by the card support 31, after which the card position correcting is released.

The support 32 is then raised by the driven vertical guide 34. The card support 31 rotates around the horizontal rotation shaft 33, and the printed rewritable card RC is moved from its horizontal state to the inclined state shown in FIG. 4 and passed to the card grippers 22a and 22b of the handling mechanism 20.

The front or back direction of the printed rewritable card RC when it is passed to the handling mechanism 20, and the front or back direction of the unprinted rewritable card RC when it is inserted into the card printing mechanism 50, are determined in advance. The card conveyance mechanism 30 flips the rewritable card RC over as needed, on the basis of information about the predetermined front and back direction, or a signal from the second card sensor 42.

1.2.3. Card Position Correcting Mechanism 40

Figure 6:
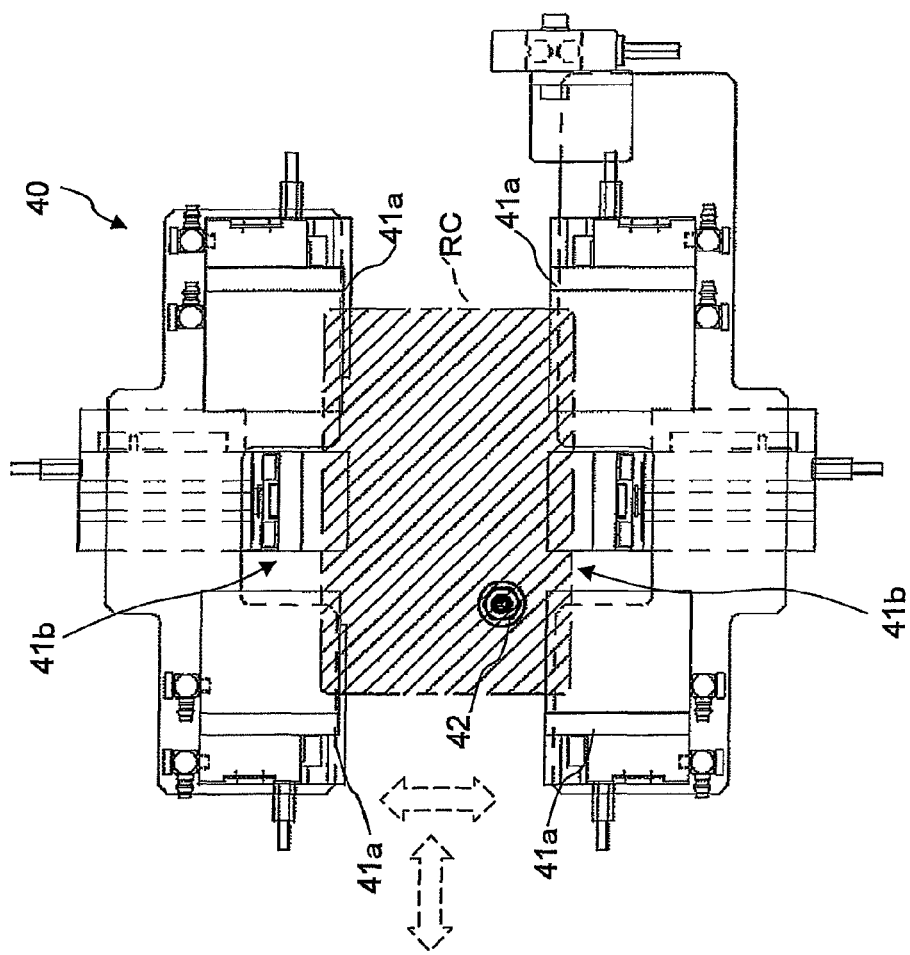
FIG. 6 is a top view of the card position correcting mechanism pertaining to this embodiment.

As shown in FIG. 6, the card position correcting mechanism 40 has first position correctors 41a, second position correctors 41b, and the second card sensor 42.

As shown by the imaginary line arrows in FIG. 6, the first position correctors 41a sandwich the corners of a rewritable card RC placed substantially in the horizontal direction, and thereby perform planar positioning of the rewritable card RC to the left and right and in the longitudinal direction. Further, the second position correctors 41b sandwich the long sides of the rewritable card RC, and thereby perform planar and lateral positioning of the rewritable card RC.

The second card sensor 42 is an optoelectric sensor having a light projecting and receiving element. For example, it is a color sensor that makes use of a three-color (red, blue, green) LED light source for a light projecting element, and that shines a spot of light on a substance and performs color discrimination by color component analysis of light received by reflection from the substance. The second card sensor 42 senses a rewritable card RC and sends a signal to the device controller 5. The device controller 5 decides from the transmitted signal whether or not a rewritable card RC is present and which way it is facing (back or front). The second card sensor 42 may also be a CCD camera, and the device controller 5 may decides whether or not a rewritable card RC is present and which way it is facing (back or front) by recognizing the obtained image.

1.2.4. Card Printing Mechanism 50

The card printing mechanism 50 produces a printed rewritable card RC by printing specific information on a rewritable card RC on the basis of patient identification information, at a command from the managing device 310.

The card printing mechanism 50 has, for example, a hot roller, a thermal head, or another such thermal energy imparting component in its interior, and thermal energy of a specific temperature is applied to the information display face of the inserted rewritable card RC, thereby erasing or writing information from or to the information display face. Rewritable card printing devices such as this are well known, and thus will not be described in detail here.

1.2.5. Card Stocker 70

The card stocker 70 holds extra rewritable cards RC.

If an unprinted rewritable card RC cannot be recovered from a tray T, that is, if an unprinted rewritable card RC cannot be supplied to the card printing mechanism 50, the device controller 5 outputs a request to the managing device 310 to supply an unprinted rewritable card RC. According to the request, the managing device 310 issues a command to the card printing mechanism 50 to supply an unprinted rewritable card RC. At this command, the card printing mechanism 50 requests a rewritable card RC from the card stocker 70. Consequently, a rewritable card RC is supplied to the card printing mechanism 50.

1.3. Label/Prescription Printing Unit 6

As shown in FIG. 7, the label/prescription printing unit 6 has a label printing mechanism 61 for printing the labels L1 and L2, a prescription printing mechanism 62 for printing prescriptions, and an insertion mechanism 63 for inserting the printed prescriptions and labels L1 and L2.

The label printing mechanism 61 is disposed above the card processing unit 10, and normally prints out drug administration labels L2 listing drug administration information, but if an error occurs in the card processing unit 10, then a tray label L1, which displays patient identification information and takes the place of the rewritable card RC, is printed in addition to the drug administration label L2.

As shown in FIG. 7, the prescription printing mechanism 62 is disposed above the label printing mechanism 61. The prescription printing mechanism 62 prints out prescriptions for each tray T according to the prescription information for each patient.

The insertion mechanism 63 moves a pocket 63a up and down. The pocket 63a accepts a prescription from the prescription printing mechanism 62, accepts a drug administration label L2 from the label printing mechanism 61, and inserts these into the tray T. The pocket 63a moves up and down according to commands from the device controller 5 upon receipt of an error signal as discussed below, accepts from the label printing mechanism 61 a tray label L1 on which has been printed the same patient identification information as that on the rewritable card RC, and inserts this into the tray T.

1.3.1. Label Printing Mechanism 61

Normally, the label printing mechanism 61 prints a drug administration label L2 according to a print command from the managing device 310. After printing, the drug administration label L2 comes out of the discharge opening of the label printing mechanism 61 and is temporarily held in a label pocket 61a, after which it goes into the pocket 63a of the insertion mechanism 63. Drug administration labels L2 are supplied to all of the trays T.

The label pocket 61a temporarily holds the drug administration label L2 printed while the pocket 63a of the insertion mechanism 63 is accepting a prescription from the prescription printing mechanism 62.

Next, the typical operation of the card processing unit 10 when an error occurs will be described.

In addition to normally printing the drug administration label L2, the label printing mechanism 61 prints a tray label L1 that is used in place of the rewritable card RC when an error occurs in the card processing unit 10. The label printing mechanism 61 in this case operates under a command from the managing device 310 to print a tray label L1, as discussed below. The tray label L1 is affixed manually to the tray T during drug inspection or the like after transport of the tray T. The tray label L1 is printed with patient identification information.

<When Error Occurs Before Printing of Drug Administration Label L2>

After the printing of the drug administration label L2 and then the printing of the tray label L1, the two labels L1 and L2 come out of the discharge opening of the label printing mechanism 61 and are temporarily held in the label pocket 61a. After this, the labels L1 and L2 are put into the pocket 63a of the insertion mechanism 63 and supplied to the tray T.

The same processing as above is also performed if the error occurs during the printing of the drug administration label L2.

<When Error Occurs after Printing of Drug Administration Label L2>

First, the drug administration label L2 is supplied to the tray T through the same processing as above. During this time, the printing of the tray label L1 is finished, after which this label comes out of the discharge opening of the label printing mechanism 61 and is temporarily held in the label pocket 61a. After this, the tray label L1 is put in the pocket 63a of the insertion mechanism 63 and supplied to the tray T.

1.3.2. Prescription Printing Mechanism 62

The prescription printing mechanism 62 prints a prescription paper listing patient identification information. The printed prescription is put in the pocket 63a of the insertion mechanism 63 and inserted into the trays T of all patients.

1.3.3. Insertion Mechanism 63

The insertion mechanism 63 has a guide G that extends in the up and down direction in FIG. 7, and the pocket 63a that moves up and down along this guide G.

The pocket 63a of the insertion mechanism 63 is disposed opposite the label printing mechanism 61 and the prescription printing mechanism 62, and is moved up and down along the guide G by a motor or other such drive source. The pocket 63a accepts the labels L1 and L2 and a prescription from the label printing mechanism 61 and the prescription printing mechanism 62, and inserts these into the tray T.

1.4. Device Controller 5 and Managing Device 310

Figure 8:
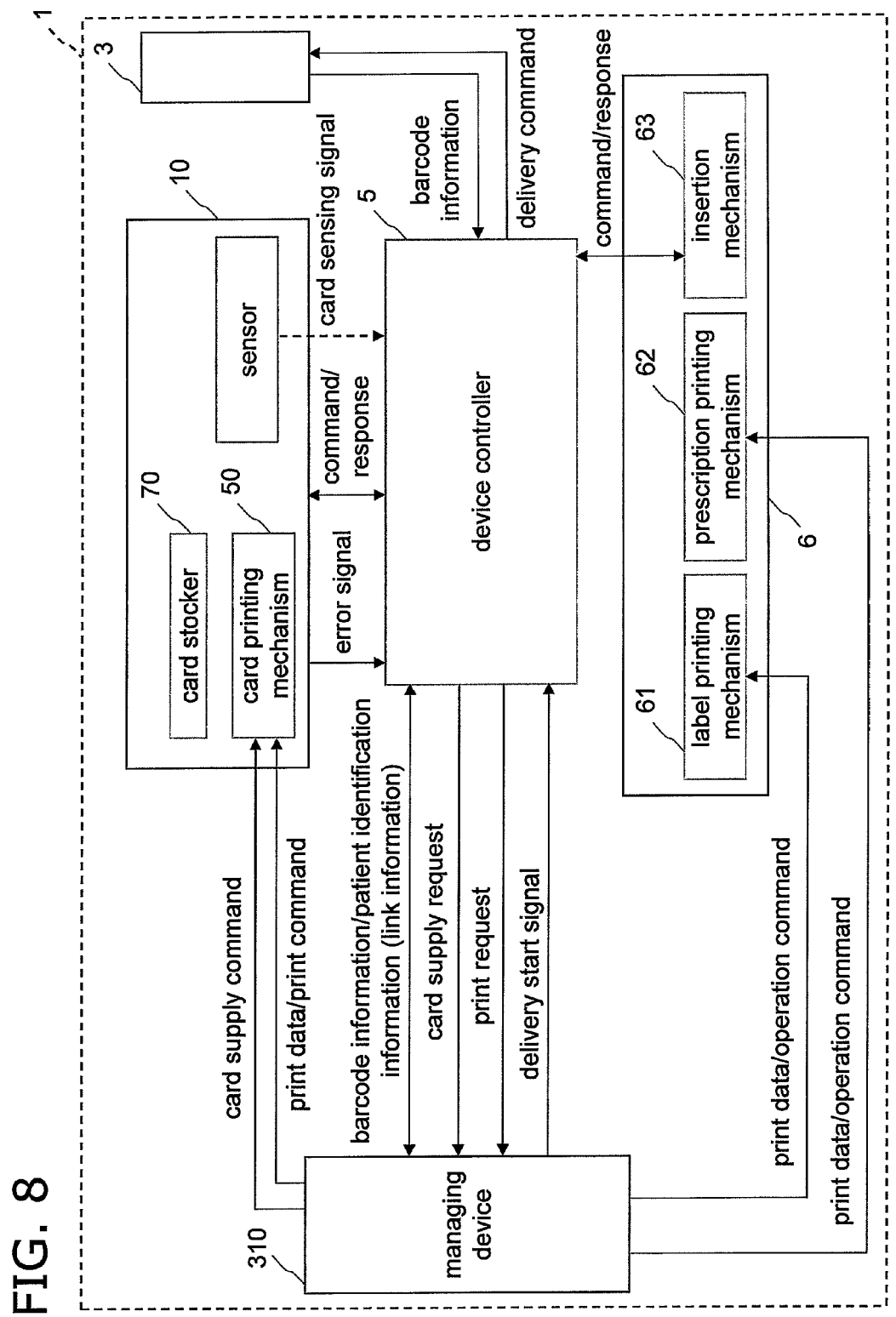
FIG. 8 is a control block diagram of the drug delivery device pertaining to this embodiment.

FIG. 8 is a control block diagram illustrating the relation between the device controller 5, the card processing unit 10, the label/prescription printing unit 6, and the managing device 310 of the drug delivery device 1.

The device controller 5 controls the operation of the various mechanisms of the label/prescription printing unit 6 and the card processing unit 10. The device controller 5 commands the operation of the label printing mechanism 61 and insertion mechanism 63 of the label/prescription printing unit 6 on the basis of specific criteria.

More specifically, the device controller 5 receives a signal that senses a rewritable card RC from sensors of the card processing unit 10 (the first card sensor 26 and third card sensor 27 of the handling mechanism 20, and the second card sensor 42 of the card position correcting mechanism 40). The device controller 5 also receives an error signal from the card processing unit 10 and sends the managing device 310 a request to print a tray label L1 or a request to supply a rewritable card RC.

The managing device 310 receives patient identification information, drug administration information, prescription information, and the like from the electronic chart system 300 (FIG. 1), and issues commands to the drug delivery device 1 on the basis of this information.

More specifically, the managing device 310 supplies rewritable cards RC through the card printing mechanism 50 to the card stocker 70 according to a request from the device controller 5 to supply rewritable cards RC. The managing device 310 outputs a command to the card printing mechanism 50 to print rewritable cards RC. The managing device 310 also outputs an operation command to the label printing mechanism 61, so that a tray label L1 is printed, according to a request from the device controller 5 to print a tray label L1.

Normally, the managing device 310 outputs an operation command for printing a drug administration label L2 to the label printing mechanism 61. The managing device 310 outputs an operation command for printing a prescription corresponding to the prescription information to the prescription printing mechanism 62.

The managing device 310 also sends and receives barcode information and patient identification information (link information) to and from the device controller 5. More specifically, the managing device 310 receives, via the device controller 5, barcode information for a tray T (tray identification information) read by a barcode reader (not shown) of the drug delivery unit 3. The managing device 310 produces link information that correlates this barcode information with drug information based on patient identification information or patient prescription information, for example, and sends this to the device controller 5. The device controller 5 stores this link information in a memory. The device controller 5 also sends a drug delivery command to the drug delivery unit 3.

1.5. Overall Flow

Figure 9:
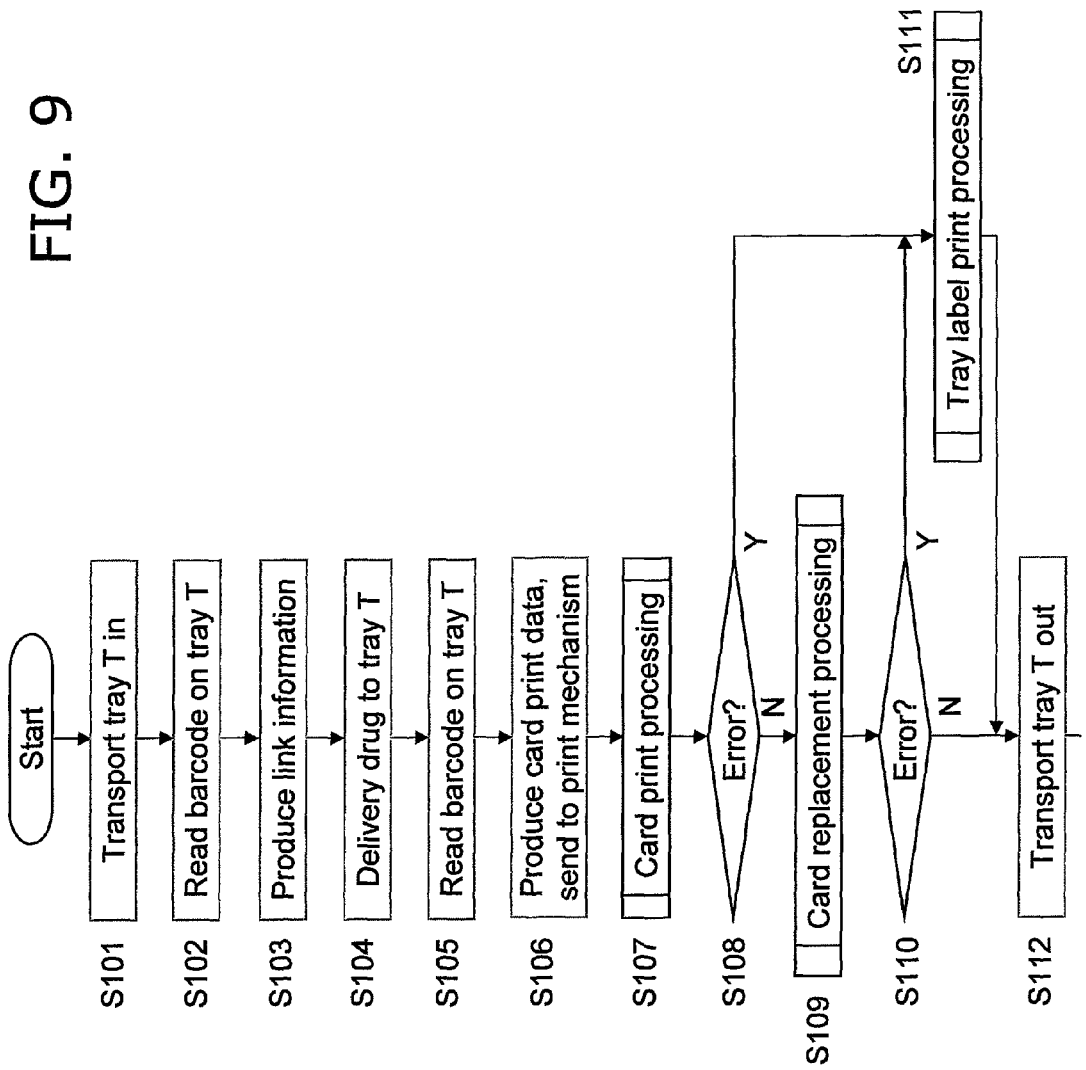
FIG. 9 is a flowchart of the overall flow of card processing and label print processing pertaining to this embodiment.

FIG. 9 shows the flow of a series of processing in which the drug delivery device 1 brings in a tray T at a command from the managing device 310, a drug is delivered, then an unprinted rewritable card RC is recovered from the tray T, a printed rewritable card RC is attached to the tray T, a prescription and a drug administration label L2 are inserted into the tray T, and the tray T is transported away. If, however, an error should occur in the course of processing related to a rewritable card RC, the processing inserts a tray label L1 instead of a printed rewritable card RC.

In this embodiment, the unprinted rewritable card RC installed ahead of time in each tray T is printed with patient identification information corresponding to the drug delivered to one subsequent tray T. Accordingly, the unprinted rewritable card RC that had been installed on each tray T is taken off, and at the same time, a printed rewritable card RC on which has been printed patient identification information corresponding to the drug delivered to that tray is installed. As a result, the standby time for the tray T is shortened, and transport efficiency is improved.

To facilitate understanding, the transport of a single tray T in and out of the drug delivery device 1 will be described below, but it is assumed that trays T are transported in one after the other and processed in parallel. Also, the following processing is just one example, and the present invention is not limited to or by the order, details, etc., thereof.

The following is premised on the production of drug information by the managing device 310 for drug delivery on the basis of a patient's prescription information.

Step S101: First, a tray T is transported from the tray supply unit 2 into the drug delivery unit 3.

Step S102: The barcode reader (not shown) of the drug delivery unit 3 reads barcode information on the tray T (tray identification information) and sends it to the managing device 310.

Step S103: The managing device 310 produces link information that correlates the above-mentioned barcode information with the above-mentioned drug information, and sends this to the device controller 5 of the drug delivery device 1. The link information is stored in a memory of the device controller 5.

Step S104: Drugs are delivered sequentially to the tray T on the basis of the drug information for that patient.

Step S105: At the point when the immediately prior drug delivery of the card processing unit 10 is completed by the drug delivery unit 3, the barcode information of that tray T is read by a barcode reader 71 (FIG. 2) and sent to the managing device 310. At this point, a request to print a rewritable card RC is issued.

Step S106: The managing device 310 produces card printing data on the basis of the patient identification information corresponding to the above-mentioned barcode information. The card printing data is outputted to the card printing mechanism 50.

Step S107: Card print processing is performed by the card processing unit 10 (steps S1001 to S1011).

Step S108: If an error signal has been issued in the card print processing, the flow moves to step S111, but if no error signal has been issued, the flow moves to step S109. The phrase "an error signal has been issued" here refers to a situation in which no rewritable card RC was supplied from the card stocker 70. Furthermore, an error signal will be issued if there is some kind of malfunction in the card processing unit 10 and a rewritable card RC cannot be printed, or if there is a problem in the printing of the rewritable card RC, or if the rewritable card RC fails to be conveyed, etc.

Step S109: The card processing unit 10 performs card replacement processing (steps S1071 to S1078).

Step S110: If an error signal has been issued in the card replacement processing, the flow moves to step S111, but if no error signal has been issued, the flow moves to step S112. The phrase "an error signal has been issued" here refers to a situation in which no printed rewritable card RC could be attached to the tray T by the handling mechanism 20. Furthermore, an error signal will be issued if there is some kind of malfunction in the card processing unit 10 and a printed rewritable card RC was not properly attached to the tray T, etc.

Step S111: Tray label L1 print processing is performed (steps S1091 to S1092).

Step S112: A tray T to which a printed rewritable card RC has been attached, or a tray T in which a tray label L1 has been inserted, is transported out.

1.5.1. Card Print Processing by Card Processing Unit 10

Figure 10:
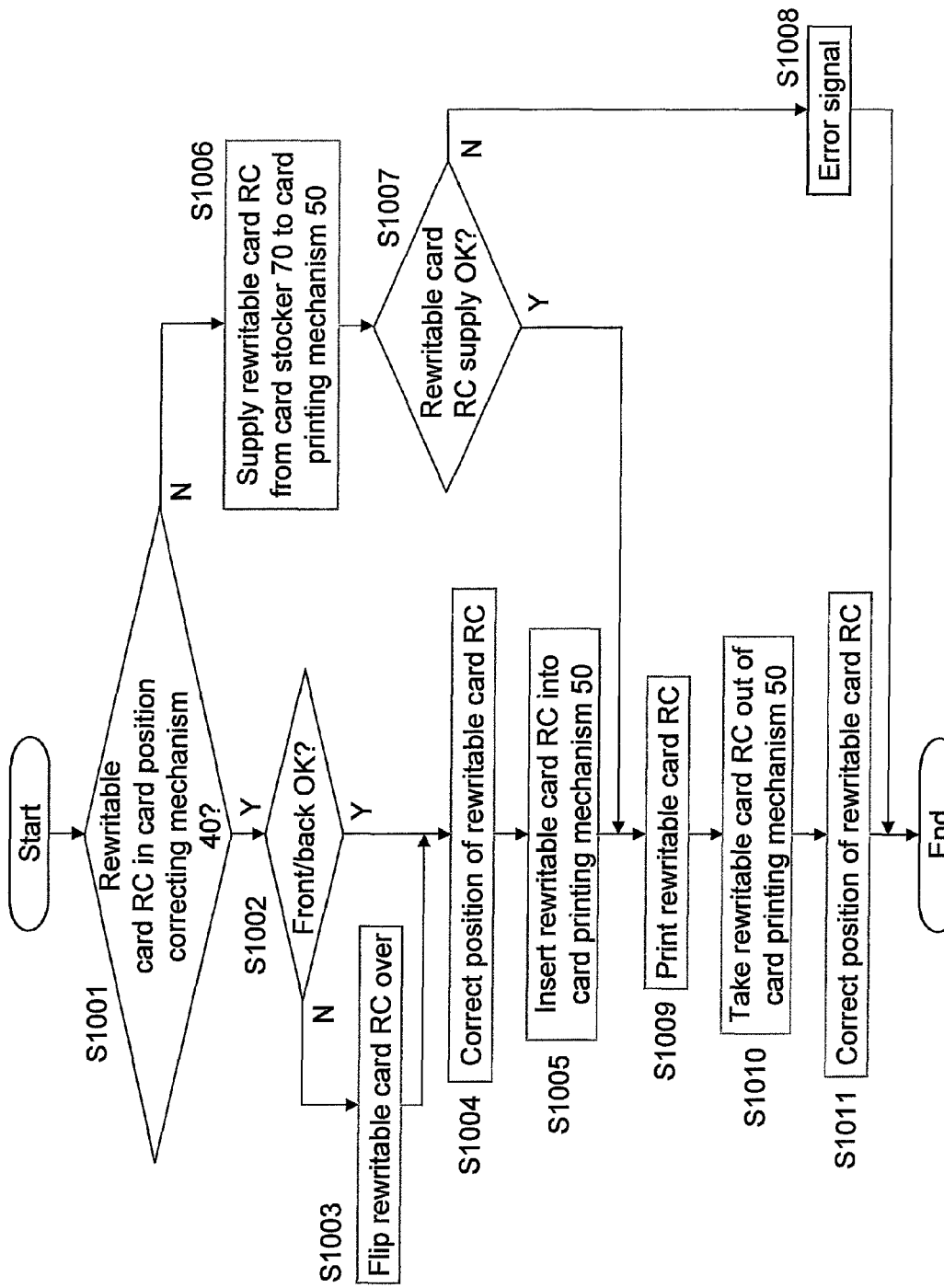
FIG. 10 is a flowchart of the card print processing of the card processing unit pertaining to this embodiment.

FIG. 10 shows the flow of card print processing by the card processing unit 10.

Step S1001: When the second card sensor 42 of the card position correcting mechanism 40 detects that a rewritable card RC has been placed in the card position correcting mechanism 40, a signal is sent to the device controller 5. If a rewritable card RC has been sensed, the flow moves to step S1002, but if no rewritable card RC has been sensed, the flow moves to step S1006.

Step S1002: The device controller 5 also determines from the signal of the second card sensor 42 which side of the rewritable card RC is the front and which is the back. If the orientation of the rewritable card RC is not what it is supposed to be, the flow moves to step S1003, but if it is as it is supposed to be, the flow moves to step S1004.

Step S1003: The card conveyance mechanism 30 flips over the rewritable card RC and puts it back in the card position correcting mechanism 40.

Step S1004: After the card conveyance mechanism 30 lets go of the rewritable card RC, the card position correcting mechanism 40 corrects the position of the rewritable card RC.

Step S1005: The card conveyance mechanism 30 grasps the position-corrected unprinted rewritable card RC and inserts it into the card printing mechanism 50.

Step S1006: On the other hand, if no rewritable card RC has been sensed by the second card sensor 42, the device controller 5 outputs a request to the managing device 310 to supply an unprinted rewritable card RC. The managing device 310 outputs a command to the card printing mechanism 50 to supply an unprinted rewritable card RC in response to this request. The card stocker 70 supplies an extra rewritable card RC to the card printing mechanism 50 in response to this command.

Step S1007: If no extra rewritable card RC could be supplied from the card stocker 70, the flow moves to step S1008, but if the extra rewritable card RC was supplied, the flow moves to step S1009.

Step S1008. The card processing unit 10 sends an error signal to the device controller 5.

Step S1009: Card printing data produced by the managing device 310 is printed on the rewritable card RC by the card printing mechanism 50.

Step S1010: The card conveyance mechanism 30 removes the rewritable card RC from the card printing mechanism 50.

Step S1011: After the card conveyance mechanism 30 has let go of the rewritable card RC, the card position correcting mechanism 40 corrects the position of the rewritable card RC. After this, the rewritable card RC is grasped by the card conveyance mechanism 30 and passed to the handling mechanism 20 (step S1072).

1.5.2. Card Replacement Processing by Card Processing Unit 10

Figure 11:
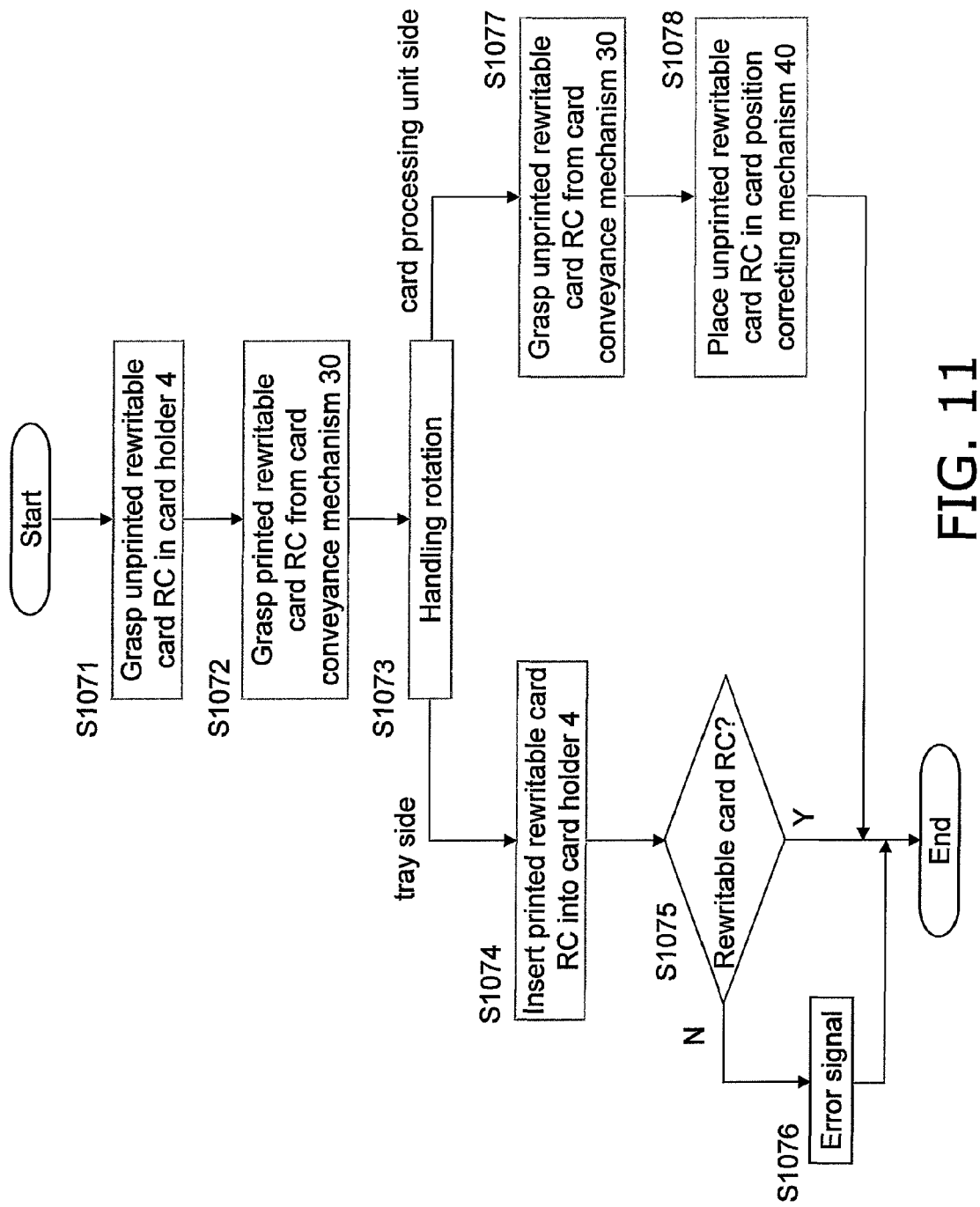
FIG. 11 is a flowchart of the card replacement processing of the card processing unit pertaining to this embodiment.

FIG. 11 shows the flow of card replacement processing by the card processing unit 10.

Step S1071: The unprinted rewritable card RC in the card holder 4 of the tray T is grasped by the card gripper 22a of the handling mechanism 20 of the card processing unit 10.

Step S1072: At the same time, the printed rewritable card RC held by the card conveyance mechanism 30 is grasped by the other card gripper 22b of the handling mechanism 20.

Step S1073: The handling mechanism 20 rotates 180 degrees. The card gripper 22a moves to the card position correcting mechanism 40 side, and the card gripper 22b to the tray T side.

Step S1074: The printed rewritable card RC is inserted by the card gripper 22b into the card holder 4 of the tray T.

Step S1075: On the tray T side, the printed rewritable card RC is sensed by the first card sensor 26, and a signal is sent to the device controller 5. Processing ends if a printed rewritable card RC is sensed, but if no printed rewritable card RC has been sensed, the flow moves to step S1076.

Step S1076: The device controller 5 issues an error signal.

Step S1077: Meanwhile, on the card position correcting mechanism 40 side, the unprinted rewritable card RC is passed by the card gripper 22a to the card conveyance mechanism 30.

Step S1078: The unprinted rewritable card RC is placed in the card position correcting mechanism 40 by the card conveyance mechanism 30.

1.5.3. Printing Processing of Tray Label L1

Figure 12:
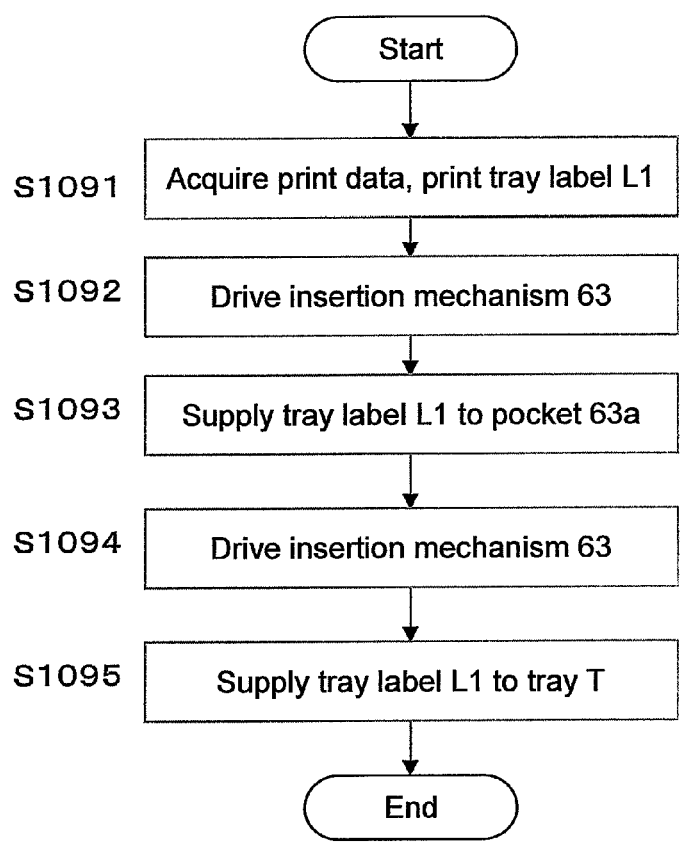
FIG. 12 is a flowchart of the tray label print processing of the label/prescription printing unit pertaining to this embodiment.
Figure 13:
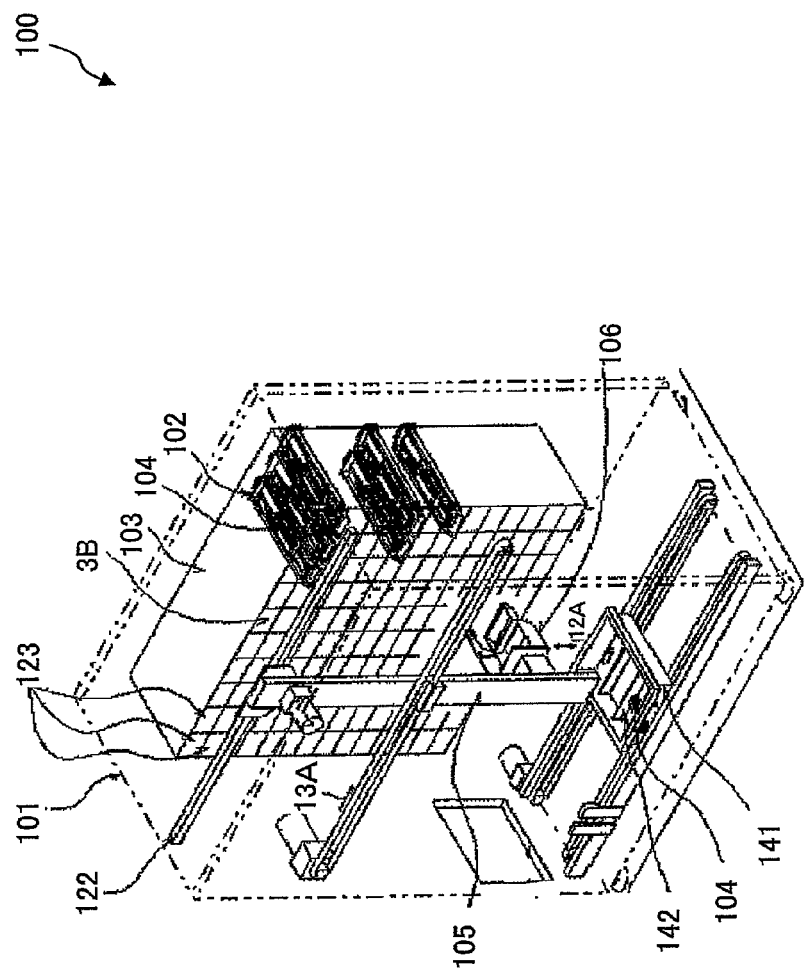
FIG. 13 is a perspective view of a conventional drug delivery device.
Figure 14:
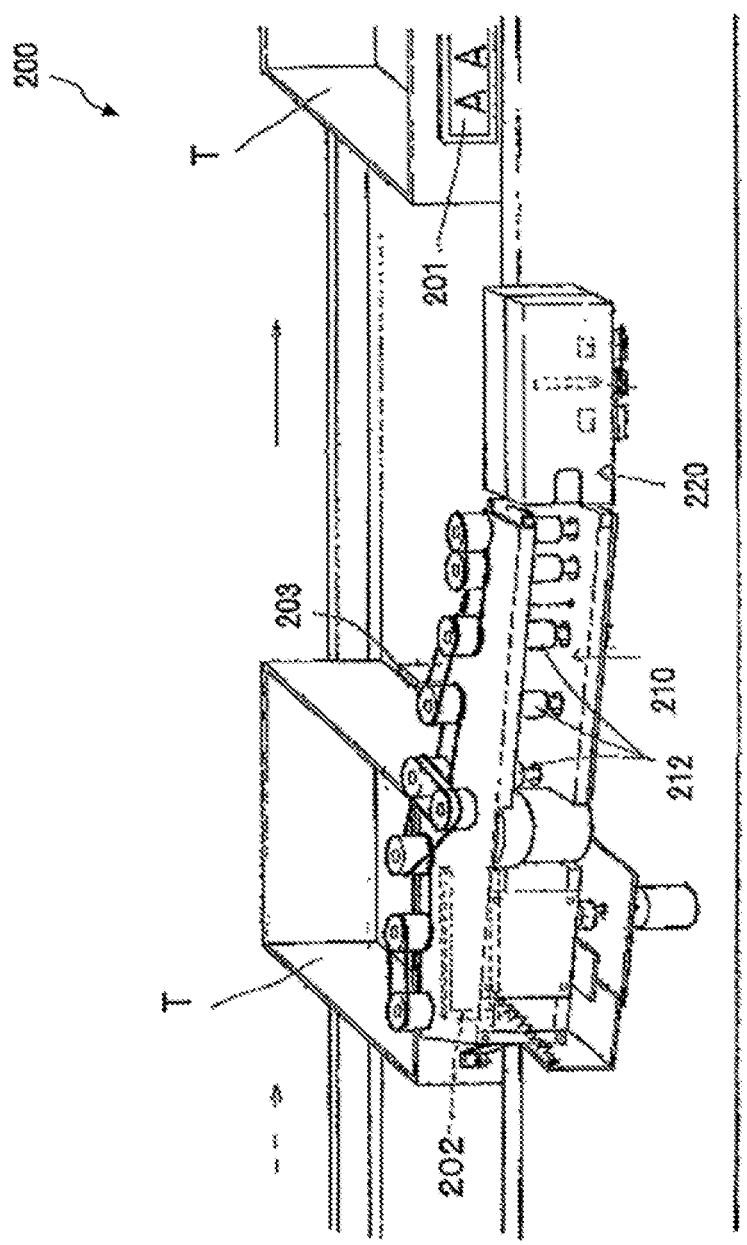
FIG. 14 is a perspective view of another conventional drug delivery device.

FIG. 12 shows the flow of print processing of the tray label L1 by the label/prescription printing unit 6.

Step S1091: The managing device 310 outputs patient identification information for the tray T in error, as tray label data, to the label printing mechanism 61 according to a request from the device controller 5 to print a tray label L1. The label printing mechanism 61 prints the tray label data to produce the tray label L1.

Step S1092: Then, the insertion mechanism 63 is driven, and the pocket 63a is aligned with the position of the label printing mechanism 61.

Step S1093: The label printing mechanism 61 supplies the tray label L1 temporarily held in the label pocket 61a to the pocket 63a of the insertion mechanism 63.

Step S1094: Next, the insertion mechanism 63 is driven until the pocket 63a reaches the position of insertion into the tray T.

Step S1095: The tray label L1 is supplied from the pocket 63a to the tray T.

Although omitted from the description of the processing above, usually the label printing mechanism 61 prints a drug administration label L2, which is inserted into the tray T by the insertion mechanism 63 along with a prescription printed by a prescription printing mechanism 62. The print processing for the tray label L1 is performed in addition to this ordinary processing when an error occurs at the card processing unit 10.

The type of error is not limited to what was described above. For instance, a tray label L1 may be printed when an error is detected as a result of an unexpected stoppage or a malfunction of one of the various mechanisms of the card processing unit 10.

1.6. Features of This Embodiment

With the drug delivery device 1 pertaining to this embodiment, the card processing unit 10 that prints a rewritable card RC to be attached to the tray T is used in parallel with the label/prescription printing unit 6 that prints a drug administration label L2 and a prescription in a normal state, and if an error occurs in the card processing unit 10, a tray label L1 is printed instead of the rewritable card RC and in addition to the drug administration label L2 by the label/prescription printing unit 6.

Thus, even though there is the possibility that a rewritable card RC will fail to be attached by the card processing unit 10, since the tray label L1 can be printed instead of the rewritable card RC, identifying information for the tray T can be provided reliably and quickly, and drug delivery efficiency can be improved.

With the drug delivery device 1 pertaining to this embodiment, an error signal is generated if no printed rewritable card RC is sensed by the first card sensor 26. Consequently, it can be reliably detected when there is a high probability of failure to attach a rewritable card RC, and a tray label L1 can be printed.

With the drug delivery device 1 pertaining to this embodiment, the card stocker 70 is provided, and if there are not enough unprinted rewritable cards RC, extra unprinted rewritable cards RC are supplied from the card stocker 70. Consequently, an inadequate supply of unprinted rewritable cards RC can be dealt with. Also, in this case no tray label L1 is printed, which prevents tray labels L1 from being printed too often.

With the drug delivery device 1 pertaining to this embodiment, a tray label L1 is printed if an error should occur in the card processing unit 10 itself. Consequently, it can be reliably detected when there is a high probability of failure to attach a rewritable card RC, and a tray label L1 can be printed.

With the drug delivery device 1 pertaining to this embodiment, since the rewritable card RC is a rewritable card, once a printed rewritable card RC is inserted into the card holder 4 of the tray T, it can still be used as an unprinted rewritable card RC for the next delivery.

2. Other Embodiments

2.1. Pattern of Selecting Label Printing

In the above embodiment, the tray label L1 is printed instead of the rewritable card RC in the following situations.

(1) When a rewritable card RC could not be printed because a rewritable card RC could not be supplied from the card stocker 70 (step S1007 in FIG. 10).

(2) When there was no rewritable card RC after attachment to the tray T (step S1075 in FIG. 11).

A tray label L1 may also be printed in the following situations.

(3) When a rewritable card RC could not be taken out of the tray T.

Whether or not a rewritable card RC has been taken out of a tray T is determined by sensing with the first and third card sensors 26 and 27 of the handling mechanism 20 or with the second card sensor of the card position correcting mechanism 40 (step S1071 in FIG. 11 or step S1001 in FIG. 10), and sending a signal to the device controller 5.

In the above case, since the card stocker 70 is provided, if a rewritable card RC could not be taken out of the tray T, a tray label L1 can be printed regardless of whether or not a rewritable card RC is supplied from the card stocker 70. Consequently, identifying information for the tray T can be applied to the tray T more reliably. Thus, this avoids the risk of not being able to identify the tray T or of mistakenly identifying the tray T, so safety is improved.

Also, the card stocker 70 needs not be provided in this case.

Also, if the tray label L1 is inserted even though a rewritable card RC was attached, a means may be provided for removing the rewritable card RC from the tray T. This prevents a rewritable card RC and a tray label L1 from being applied to the tray T redundantly. Also, the card can be removed for the sake of safety when the wrong information is displayed on a rewritable card RC processed by the card processing unit 10, or when the wrong rewritable card RC has been attached, for example.

2.2. Using Both Card Printing and Tray Label Printing

In the above embodiment, a tray label L1 is printed instead of printing a rewritable card RC, but both a printed rewritable card RC and a tray label L1 may be printed. This provides a means for reliably identifying a patient, for example, even when the printed rewritable card RC should be dropped off or the like along the transport path P.

2.3. Controller

In the above embodiment, the device controller 5 and the managing device 310 were provided as controllers, but the present invention is not limited to this mode. All or part of the control of each may be performed by another device, or a single device may be provided, either integrally or as a separate unit, and handle all of the control.

2.4. Card Sensor

The position of the first card sensor 26 and the third card sensor 27 of the handling mechanism 20 of the card processing unit 10, and the position of the second card sensor 42 of the card position correcting mechanism 40 are not limited to those in the above embodiment.

Also, the number of card sensors may be just one, or may be three or more. Also, the device controller 5 may decide whether or not there is an unprinted rewritable card RC or a printed rewritable card RC on the basis of signals from a plurality of card sensors at different locations.

2.5. Card Attachment to Conveyance Receptacle

In the above embodiment, the tray T (conveyance receptacle) was transported in a state in which the rewritable card RC was already attached, but instead of this, the rewritable card RC supplied from the card stocker 70 or the like may be attached by the card processing unit 10.

INDUSTRIAL APPLICABILITY

The present invention is useful as a drug delivery device and a drug delivery method because it has the effect of applying identification information reliably and quickly to a conveyance receptacle by which a drug is to be delivered, and improving the drug delivery efficiency.

EXPLANATION OF REFERENCE 1 drug delivery device
2 tray supply unit
3 drug delivery unit
4 card holder
5 device controller (controller)
6 label/prescription printing unit (label printer)
61 label printing mechanism
61a label pocket
62 prescription printing mechanism
63 insertion mechanism
63a pocket
7 completed tray stacking unit
10 card processing unit (card processor)
20 handling mechanism
21 arm
22a, 22b card gripper
23a, 23b support
24a, 24b guide
25 vertical rotation shaft
26 first card sensor (card detector)
27 third card sensor (card detector)
30 card conveyance mechanism
31 card support
32 support
33 horizontal rotation shaft
34 vertical guide
35 longitudinal guide
40 card position correcting mechanism
41a first position corrector
41b second position corrector
42 second card sensor (card detector)
50 card printing mechanism
70 card stocker
71 barcode reader
300 electronic chart system
310 managing device (controller)
G guide (for insertion mechanism 63)
L1 tray label (first label)
L2 drug administration label (second label)
P tray transport path
RC rewritable card (card)
T tray (conveyance receptacle)

What is claimed is:

1. A drug delivery device that delivers a stored drug to a conveyance receptacle adapted to be attached with a card that displays desired information, said drug delivery device comprising:

a card processor configured to enter patient identification information on the card and attach the card to the conveyance receptacle;
a label printer configured to print a first label configured to display the patient identification information and to be put into the conveyance receptacle; and
a controller configured to cause the label printer to print the first label according to a state of the card processor,
wherein the card processor includes a card detector configured to detect the card at a specific location, and
wherein the controller causes the label printer to print the first label when the detector has not detected any card at the specific location.

2. The drug delivery device according to claim 1, wherein the card is a rewritable card.

3. The drug delivery device according to claim 1, wherein the label printer further prints a second label configured to display the patient identification information and drug administration information and to be put into all conveyance receptacles including the conveyance receptacle.

4. The drug delivery device according to claim 1, wherein the controller causes the label printer to print the first label when an error occurs in the card processor.

5. The drug delivery device according to claim 1, further comprising a card holder configured to hold extra cards to be supplied to the card processor,
wherein the controller supplies the extra cards to the card processor from the card holder.

6. The drug delivery device according to claim 5, wherein the controller does not cause the label printer to print the first label when any of the extra cards is supplied.

7. The drug delivery device according to claim 5, wherein the controller causes the label printer to print the first label when any of the extra cards is supplied.

8. The drug delivery device according to claim 1, further comprising a unit configured to remove the card attached to the conveyance receptacle onto which the first label has been printed by the label printer.

9. A drug delivery method of delivering a stored drug to a conveyance receptacle adapted to be attached with a card that displays desired information, said drug delivery method comprising:

performing a card processing of entering patient identification information on the card and attaching the card to the conveyance receptacle;
performing a label printing of printing a first label configured to display the patient identification information and to be put into the conveyance receptacle; and
performing a controlling of executing said performing of the label printing to cause the first label to be printed according to a state of said performing of the card processing,
wherein said performing of the card processing includes detecting the card at a specific location, and
wherein said performing of the controlling includes executing said performing of the label printing to cause the first label to be printed when any card at the specific location has not been detected in said performing of the card processing.

* * * * *